United States Patent [19]
Von Deyn et al.

[11] Patent Number: 5,162,376
[45] Date of Patent: Nov. 10, 1992

[54] ALKYLBENZENES FOR COMBATING NEMATODES

[75] Inventors: Wolfgang Von Deyn, Neustadt; Jochen Wild, Ruppertsberg; Peter Hofmeister, Neustadt; Uwe Kardorff, Mannheim; Christoph Kuenast, Otterstadt, all of Fed. Rep. of Germany

[73] Assignee: BASF Aktiengesellschaft, Ludwigshafen, Fed. Rep. of Germany

[21] Appl. No.: 706,421

[22] Filed: May 24, 1991

[30] Foreign Application Priority Data

May 31, 1990 [DE] Fed. Rep. of Germany ....... 4017573

[51] Int. Cl.$^5$ ............................................. A01N 27/00
[52] U.S. Cl. ................................................... 514/764
[58] Field of Search ........................................ 514/764

[56] References Cited

U.S. PATENT DOCUMENTS

| 2,769,745 | 11/1956 | Hardy | 167/39 |
| 3,686,419 | 8/1972 | Duyfjes et al. | 514/764 |
| 4,556,679 | 12/1985 | Koehler | 514/764 |

Primary Examiner—Allen J. Robinson
Attorney, Agent, or Firm—Keil & Weinkauf

[57] ABSTRACT

Methods of combating nematodes or of preventing crop plants from being attacked by nematodes, wherein an effective amount of an alkylbenzene of the general formula I

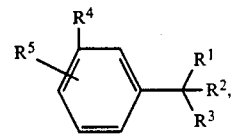

where
$R^1$, $R^2$ are each $C_1$–$C_4$-alkyl;
$R^3$ is $C_1$–$C_6$-alkyl, $C_3$–$C_6$-cycloalkyl, $C_2$–$C_4$-alkenyl or $C_2$–$C_4$-alkynyl;
$R^4$ is hydrogen, $C_1$–$C_6$-alkyl or $C_2$–$C_4$-alkenyl; and
$R^5$ is $C_1$–$C_6$-alkyl, $C_3$–$C_6$-cycloalkyl, $C_2$–$C_4$-alkenyl or $C_2$–$C_4$-alkynyl is allowed to act on the pests or their habitat, and the use of alkylbenzenes of the formula I for combating nematodes.

2 Claims, No Drawings

ALKYLBENZENES FOR COMBATING NEMATODES

The present invention relates to a process for combating nematodes, or for preventing crop plants from being attacked by nematodes, wherein an effective amount of an alkylbenzene of the general formula I

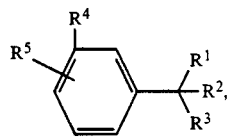

where $R^1$ und $R^2$ are $C_1$–$C_4$-alkyl; $R^3$ is $C_1$–$C_6$-alkyl, $C_3$–$C_6$-cycloalkyl, $C_2$–$C_4$-alkenyl or $C_2$–$C_4$-alkynyl; $R_4$ is hydrogen, $C_1$–$C_6$-alkyl or $C_2$–$C_4$-alkenyl; and $R^5$ is $C_1$–$C_6$-alkyl, $C_3$–$C_6$-cycloalkyl, $C_2$–$C_4$-alkenyl or $C_2$–$C_4$-alkynyl, and especially of 1-tert-butyl-3,5-dimethylbenzene, is allowed to act on the pests or their habitat.

The control of nematodes is gaining in importance, because today's intensive utilization of crop areas, especially for vegetables and ornamentals, can lead to a marked increase in these harmful pathogens (R. Heitefuβ, Pflanzenschutz, Thieme, 2nd edition, 1987).

However, the nematocides used today in agriculture and horticulture have a high toxicity to warm bloods (Pestic. Sci. 28, 331 (1990)) and are therefore not an ideal solution with regard to protection for the user.

The object of the present invention was therefore to find an effective and safe method of combating nematodes.

We have found that the above-defined alkylbenzenes of the general formula I, especially 1-tert-butyl-3,5-dimethylbenzene, are suitable for combating nematodes.

The compounds of the general formula I are known. Some of them are commercially available; others may be prepared by prior art methods of electrophilic alkylation of aromatic compounds, as described for instance in the following literature:

J. March, Advanced Organic Chemistry, Wiley, 3rd edition 1985

Houben-Weyl, Methoden der Organischen Chemie, vol. v72b, Thieme 1981.

In general formula I the substituents may for example have the following meanings:

$R^1$, $R^2$ are identical or different and each is alkyl, such as methyl, ethyl, propyl, 1-methylethyl, butyl, 1-methylpropyl, 2-methylpropyl and 1,1-dimethylethyl, especially methyl;

$R^3$ is alkyl as stated for $R^1$, and pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2,-trimethylpropyl, 1-ethyl-1-methylpropyl, especially methyl;

cycloalkyl such as cyclopropyl, cyclobutyl, cyclopentyl and cyclohexyl;

alkenyl such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl and 2-methyl-2-propenyl, or alkynyl such as ethynyl, 1-propynyl, 2-propynyl, 1-butynyl, 2-butynyl, 3-butynyl and 1-methyl-2-propynyl;

$R^4$ is hydrogen;

alkyl as stated for $R^3$, especially methyl, or alkenyl as stated for $R^3$;

$R^5$ is one of the substituents given for $R^3$, especially methyl.

Not only do the alkylbenzenes I have a nematocidal effect—they also have favorable toxicological properties (N. I. Sac, R. J. Lewis, Dangerous Properties of Industrial Materials, 7th edition, 1989).

Examples from the nematodes class are root-knot nematodes, e.g., *Meloidogyne hapla, Meloidogyne incognita* and *Meloidogyne javanica*, cyst-forming nematodes, e.g., *Globodera rostochiensis, Heterodera avenae, Hetrodera glycinae, Heterodera schachtii* and *Heterodera trifolii*, and stem and leaf eelworms, e.g., *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi*.

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorbenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The active ingredient concentrations in the finished formulations may be vary over a wide range. Generally, they are from 0.0001 to 10, and preferably from 0.01 to 1, %.

The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.2 to 10, particularly from 0.5 to 6, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

SYNTHESIS EXAMPLES

The manufacture of 1-tert-butyl-3,5-dimethylbenzene is described for instance in J. M. A. Bass et al, Trav. Chim. Pays-Bas, 88, 1110 (1969). Using different starting materials, the directions given there may be employed to obtain further alkylbenzenes I. If other synthesis methods were used, the appropriate literature references are given at the compounds listed in the table which follows.

TABLE

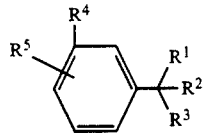

I ($R^1 = R^2 =$ methyl)

| Ex. no. | $R^3$ | $R^4$ | $R^5$ | Physical data | Lit. |
|---|---|---|---|---|---|
| 1.001 | methyl | H | 2-methyl | bp. 200° C. | 1) |
| 1.002 | methyl | H | 3-methyl | bp. 189° C. | 1) |
| 1.003 | methyl | H | 4-methyl | bp. 192° C. | 1) |
| 1.004 | methyl | H | 3-ethyl | bp. 205° C. | 1) |
| 1.005 | methyl | H | 4-ethyl | bp. 207° C. | 1) |
| 1.006 | methyl | H | 4-(1-methylethyl) | bp. 90° C. | |
| 1.007 | methyl | H | 4-butyl | bp. 241° C. | 1) |
| 1.008 | methyl | H | 4-(1-methylpropyl) | bp$_9$ 102° C. | |
| 1.009 | methyl | H | 4-(1,1-dimethylethyl) | mp. 70° C. | |
| 1.010 | methyl | H | 3-(1,1-dimethylethyl) | bp$_{18}$ 106° C. | 1) |
| 1.011 | methyl | H | 4-(1,1-dimethylethyl) | mp. 35° C. | |
| 1.012 | methyl | H | 4-(1,3,3-trimethylbutyl) | bp$_2$ 103° C. | 2) |
| 1.013 | methyl | H | 4-(1,1,3,3-tetramethylbutyl) | bp. 249° C. | 1) |
| 1.014 | methyl | H | 4-(2-propenyl) | bp$_{29}$ 120° C. | 3) |
| 1.015 | methyl | H | 4-(2-methylpropenyl) | bp$_2$ 75° C. | 1) |
| 1.016 | methyl | H | 4-(1-methylethenyl) | bp$_3$ 85° C. | 2) |
| 1.017 | methyl | H | 2-(2-propynyl) | bp$_3$ 86° C. | 4) |
| 1.018 | methyl | H | 4-(2-propynyl) | bp$_{.10}$ 102° C. | 4) |
| 1.019 | methyl | H | 4-(1-propynyl) | mp. 38° C. | 5) |
| 1.020 | methyl | H | 4-cyclopropyl | bp. 240° C. | 6) |
| 1.021 | methyl | H | 4-cyclohexyl | bp$_{.9}$ 148° C. | 8) |
| 1.022 | methyl | methyl | 5-methyl | bp$_{.21}$ 98° C. | 1) |
| 1.023 | methyl | methyl | 6-methyl | bp. 217° C. | 1) |
| 1.024 | methyl | methyl | 4-methyl | bp$_{.7}$ 80° C. | |
| 1.025 | methyl | methyl | 4-ethyl | bp$_{.3}$ 71° C. | 9) |
| 1.026 | methyl | methyl | 4-(1-methylethyl) | bp. 235° C. | 1) |
| 1.027 | methyl | methyl | 5-(1,1-dimethylethyl) | mp. 30° C. | |
| 1.028 | methyl | ethyl | 3-(1,1-dimethylethyl) | bp$_{20}$ 130° C. | 1) |
| 1.029 | methyl | 1-methylethyl | 6-methyl | bp. 237° C. | 1) |
| 1.030 | methyl | ethynyl | 5-(1,1-dimethylethyl) | mp. 87° C. | 10) |
| 1.031 | methyl | 1,1-dimethylethyl | 5-(1,3,3-trimethylbutyl) | bp. $_{2.5}$ 113° C. | 2) |
| 1.032 | methyl | 1,1-dimethylethyl | 5-(1,1-dimethylethyl) | mp. 72° C. | |
| 1.033 | ethyl | H | 4-ethyl | bp. 229° C. | 1) |
| 1.034 | ethyl | H | 3-methyl | bp. 210° C. | 1) |
| 1.035 | ethyl | methyl | 5-methyl | bp. 225° C. | 1) |

TABLE-continued $$\underset{\substack{R^5 \\ }}{\overset{R^4}{\bigcirc}}\!\!\!\begin{array}{c}R^1\\-R^2\\R^3\end{array}$$ I ($R^1 = R^2$ = methyl)

| Ex. no. | $R^3$ | $R^4$ | $R^5$ | Physical data | Lit. |
|---|---|---|---|---|---|
| 1.036 | ethyl | methyl | 4-methyl | bp.$_{35}$ 128° C. | 7) |
| 1.037 | 2,2-dimethylpropyl | methyl | 4-methyl | bp. 267° C. | 1) |

Literature

1) Beilstein, 3rd and 4th supplement, vol. V
2) G. Fraenkel et al., J. Amer. Chem. Soc., 95, 3208 (1973)
3) Int. J. Chem. Kinetics 14, 351 (1982)
4) N. M. Libman et al., Zh. Org. Chim. 15, 125, 2375 (1979)
5) I. N. Demnin et al., ibid. 14, 2323 (1978)
6) In. S. Shabarow et al., ibid. 10, 1681 (1974)
7) In. V. Pozdnyakovica et al., ibid. 23, 154 (1987)
8) S. V. Zargorodnii et al., Uhr. Khim. Zhur., 35, 374 (1969)
9) M. S. Newman et al., J. Org. Chem., 37, 4469 (1972)
10) H. Tashiro et al., J. Chem. Soc. Perkin Trans. 1, 176 (1979)

USE EXAMPLES

The nematocidal action of the alkylbenzenes of the general formula I is illustrated by the following experiments:

The following formulations were used:

a) a 0.1% solution of the active ingredient in acetone, which was further diluted with acetone according to the stated dosage rates;

b) a 10% emulsion of the active ingredient in a mixture consisting of 70 wt % of cyclohexanone, 20 wt % of Nekanil® LN (≙Lutensol® AP6, a spreader-sticker with an emulsifying and dispersing action based on ethoxylated alkylphenols) and 10 wt % of Emulphor® EL (≙Emulan® EL, an emulsifier based on ethoxylated fatty alcohols). The concentrations given in the examples were obtained by diluting the formulated active ingredient with water.

Each of the experiments described below was carried out twice.

EXAMPLE A

Inhibition of the activity of *Ditylenchus dipsaci* (bulb eelworm)

1 ml of a nematode suspension (about 100 Ditylenchus) was introduced into a 10 ml penicillin flask, and 1 ml of the aqueous active ingredient formulations was added. The inhibition of activity was assessed under the microscope after 24 hours.

2 ppm of compound no. 1.001 resulted in 80% inhibition.

EXAMPLE B 5 ml of dry quartz sand was filled into 10 ml glass vessels. 1 ml of a suspension containing about 400 nematodes was pipetted onto the sand. A further ml of a formulation of the candidate active ingredient was added. This amount of water just moistened the sand. After 24 hours' incubation at room temperature, a 1 cm long section from the stem of a bean plant (Vicia faba) was buried a few millimeters deep in the sand.

After a further 24 hours, the L 4 larvae of *Ditylenchus dipsaci* had penetrated the plant tissue and were in the lowest 10 mm of the bean stem. The sand adhering to the stem was rinsed off, the lower 10 mm section was cut off and split lengthwise. These pieces were placed for 24 hours in a dish with 5 ml of water to extract the nematodes and count them. An untreated piece of stem yielded about 100 nematodes after this procedure.

1 ppm of compound no. 1.001 achieved 80% kill.

EXAMPLE C

Action on *Meloidogyne incognita* (root-knot nematodes)

Tomato seedlings were planted in compost heavily infested with nematodes, and kept there for 3 weeks. The plants were then removed, the roots were rinsed and the plants placed for 60 minutes in aqueous formulations of the active ingredients. The seedlings were then planted separetely in sterilized soil in plastic pots 9 cm in diameter. Nematode growth and root attack were assessed after 6 to 8 weeks.

Down to 40 ppm of compound no. 1.001 inhibited root attack.

We claim:

1. A method of combating nematodes or of preventing crop plants from being attacked by nematodes which comprises: contacting the nematodes or their habitat with an amount sufficient to combat the nematodes of an alkylbenzene of the formula I

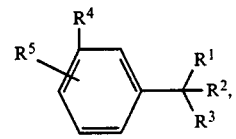

where $R^1$ and $R^2$ are each $C_1$–$C_4$-alkyl;

$R^3$ is $C_1$–$C_6$-alkyl, $C_3$–$C_6$-cycloalkyl, $C_2$–$C_4$-alkenyl or $C_2$–$C_4$-alkynyl;

$R^4$ is hydrogen, $C_1$–$C_6$-alkyl or $C_2$–$C_4$-alkenyl; and $R^5$ is $C_1$–$C_6$-alkyl, $C_3$–$C_6$-cycloalkyl, $C_2$–$C_4$-alkenyl or $C_2$–$C_4$-alkynyl.

2. The method of claim 1, where the alkylbenzene is 1-tert-butyl-3,5-dimethylbenzene.

* * * * *